(12) United States Patent
Park et al.

(10) Patent No.: US 8,518,898 B2
(45) Date of Patent: Aug. 27, 2013

(54) CYTOPROTECTIVE COMPOSITION COMPRISING HESPERIDIN OR PHARMACEUTICALLY ACCEPTABLE SALT THEREOF AS AN ACTIVE INGREDIENT

(75) Inventors: Sang Hyun Park, Jeonggeup-si (KR); Kannampalli Pradeep, Jeongeup-si (KR); Kyong Cheol Ko, Jeongeup-si (KR)

(73) Assignee: Korea Atomic Energy Research Institute, Daejeon (KR)

( * ) Notice: Subject to any disclaimer, the term of this patent is extended or adjusted under 35 U.S.C. 154(b) by 426 days.

(21) Appl. No.: 12/208,643

(22) Filed: Sep. 11, 2008

(65) Prior Publication Data

US 2009/0227526 A1    Sep. 10, 2009

(30) Foreign Application Priority Data

Mar. 4, 2008 (KR) ................. 10-2008-0020127

(51) Int. Cl.
*A61K 31/70* (2006.01)
(52) U.S. Cl.
USPC ............................................. 514/27; 514/33
(58) Field of Classification Search
USPC .......................................................... 514/27
See application file for complete search history.

(56) References Cited

U.S. PATENT DOCUMENTS 7,033,606 B1 *  4/2006  Besse et al. ............... 424/435
2004/0238781 A1 * 12/2004  Landauer et al. ............. 252/1

FOREIGN PATENT DOCUMENTS

| KR | 1019990000001 | 1/1999 |
| KR | 1019990039368 | 6/1999 |
| KR | 1999-0076178 | 10/1999 |
| KR | 1020000058219 | 9/2000 |

OTHER PUBLICATIONS

Hosseinimehr, S.J. et al, "Radioprotective effects of hesperidin against gamma irradiation in mouse bone marrow cells", The British Journal of Radiology, 79 (2006), pp. 415-418.*
M. Meister "The Health Effects of Low-Level Radiation", American council on Science and Health, New York, 2005 pp. 2-4.
M.P. Little "Cancer After Exposure to Radiation in the Course of Treatment for Benign and Malignant Disease", Lancet Oncology vol. 2, Apr. 2001 pp. 212-220.
J.F. Weiss "Protection Against Ionizing Radiation by Antioxidant Nutrients and Phytochemicals", Toxicology, 189 (2003) pp. 1-20.
J.M. Mates "Role of Reactive Oxygen Species in Apoptosis: Implications for Cancer Therapy", The International Journal of Biochemistry & Cell Biology 32 (2000) pp. 157-170.
F.A.A. Van Acker "Flavonoids Can Replace a-Tocopherol as an Antioxidant" FEBS Letters 473 (2000) pp. 145-148.

* cited by examiner

*Primary Examiner* — Elli Peselev
(74) *Attorney, Agent, or Firm* — Lucas & Mercanti, LLP

(57) ABSTRACT

Disclosed is a cytoprotective composition comprising hesperidin or a pharmaceutically acceptable salt thereof as an active ingredient. Having the ability to protect cells from radiation-induced injuries in addition to being non-toxic to cells, hesperidin in accordance with the present invention can be used as an active cytoprotective agent.

12 Claims, 10 Drawing Sheets

CYTOPROTECTIVE COMPOSITION COMPRISING HESPERIDIN OR PHARMACEUTICALLY ACCEPTABLE SALT THEREOF AS AN ACTIVE INGREDIENT

CROSS-REFERENCE TO RELATED APPLICATIONS

This patent application claims the benefit of priority from Korean Patent Application No. 10-2008-0020127, filed on Mar. 4, 2008, the contents of which are incorporated herein by reference in its entirety.

BACKGROUND OF THE INVENTION

1. Field of the Invention

The present invention relates to a composition for protecting cells against radiation, comprising hesperidin or pharmaceutically acceptable salts thereof as an active ingredient.

2. Description of the Related Art

Humans are incessantly exposed to ionizing radiation, such as cosmic rays and radiation emitted from naturally occurring radioactive species or various artificial sources. Ionizing radiation now finds a broad range of applications in various industries including electric power production, development of new, various high-yield crops, sterilization, and elongation of food shelf life (food radiation). In fact, the wide application of ionizing radiation makes exposure thereto unavoidable for humans.

Also, ionizing radiation is a powerful weapon in the treatment of various cancers because of the ability thereof to eliminate tumors or inhibit the growth of cancer cells. are treated by radiotherapy. Despite the excellent therapeutic index thereof, however, radiotherapy may give rise to damaging the normal tissue of persons surviving cancer [Meister, M., 2005. In: The health effects of low-level radiation. American Council on Science and Health, New York, pp. 2-4]. Radiotherapy has made significant contributions to the treatment of cancer and thus the life extension of cancer patients, but many of the patients who have undergone radiotherapy are found to develop secondary cancers some of which are far severer than the primary cancer was [Littler M. P., 2001. Cancer after exposing to radiation in the course of treatment for the benign and malignant disease. Lancet Oncol. 2, 212-220].

Therefore, there is an imperative need for a method by which cells can be protected from injury due to exposure to radiation.

Some studies reported that cell damage by ionizing radiation is dominantly mediated by free radicals and produced reactive oxygen species [Weiss, J. F., Landauer, M. R., 2003. Protection against ionizing radiation by antioxidant nutrients and phytochemicals, Toxicology. 189, 1-20]. Ionizing radiation ionizes water, an important cell constituent, into primary water radical species. The primary radical species created during the decomposition under radiation of water reacts with molecules to form secondary radical species such as $H_2O_2$ and $O_2^-$, which are transferred to cellular targets, such as DNA, proteins and membranes, leading to the activation of several proto-oncogenes or to cell death [Mates, J. M., Sanchez-Jimenez, F. M., 2000. Role of reactive oxygen species in apoptosis: implications for cancer therapy. *Int J Biochem Cell Biol.* 32, 157-170]. Because free radicals play an important role in the initiating and progressing of radiation-induced toxicity, the use of antioxidants in foods or as therapeutics may prevent radiation-induced injuries to cells. Recently, studies have been conducted into the potential use of flavonoids as free radical scavengers for the prevention of oxidative damage [Van Acker, F. A., Schouten, O., Haenen, R. M., van der Vijh, W. J. F., Bast, A., 2000. Flavonoid can replace tocopherol as an antioxidant. FEBS Lett. 473, 145-148].

Hesperidin (hesperetin-7-rhamnoglucoside) is a flavonoid having a molecular formula of $C_{28}H_{34}O_{15}$ with a molecular weight of 610. It has a pale yellow or yellowish appearance as a crystal or crystalline powder and gives neither scent nor taste. The flavonoid hesperidin is a flavanone glycoside (glucoside) comprised of the flavanone (a class of flavonoids) hesperitin and the disaccharide rutinose. Citrus fruits such as lemons and oranges, particularly unripe fruits, are abundant in hesperidin. The peel and membranous parts of these fruits have the highest hesperidin concentrations which amount to 1.5~3%. This flavonoid is found in green vegetables, as well. Hesperidin is thought to reduce capillary permeability and was known as vitamin P. In vivo, hesperidin has antioxidant, anti-inflammatory, hypolipidemic, vasoprotective and anti-carcinogenic and cholesterol lowering actions. Hesperidin improves the health of capillaries by increasing capillary resistance and reducing capillary permeability. Hesperidin is used to reduce hay fever and other allergic conditions by inhibiting the release of histamine from mast cells. The possible anti-cancer activity of hesperidin could be explained by the inhibition of polyamine synthesis. Some studies have showed that hesperidin added to the diet not only lowered serum and hepatic cholesterol, but also inhibited bone loss by decreasing osteoclast number in ovariectomized mice. According to the reports of other studies, hesperidin was observed to have great positive effects on the removal of the contaminant cadmium through feces, significantly lower blood glyceride and cholesterol levels and significantly increase blood HDL-cholesterol.

With regard to hesperidin, a composition for inhibiting platelet aggregation containing hesperidin or hesperetin is disclosed in Korean Patent No. 276979, a cosmetic containing alpha-glycosyl hesperidin in Korean Patent No. 184244, and a composition for lowering blood pressure in Korean Patent Application Laid-Open Publication No. 1999-0039368. Nowhere so far has the cytoprotective activity of hesperidin against radiation been mentioned in the prior art.

Leading to the present invention, intensive and thorough research into the protection of cells from radiation-induced injuries, conducted by the present inventors, resulted in the finding that hesperidin is cytoprotective against radiation.

SUMMARY OF THE INVENTION

It is therefore an object of the present invention to provide a pharmaceutical composition for protecting cells against radiation-induced injuries.

It is another object of the present invention to provide a method for protecting normal cells of a subject undergoing radiation therapy against radiation-induced injuries.

The first object of the present invention may be accomplished by provision of a cytoprotective composition comprising hesperidin or a pharmaceutically acceptable salt thereof as an active ingredient.

The second object of the present invention may be accomplished by provision of a method comprising administering the cytoprotective composition in an effective amount to a subject in need thereof.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a graph showing changes in the hepatic aspartate transaminase (AST) level of rats treated with hesperidin after exposure to various doses of gamma radiation in accordance with an embodiment of the present invention.

DESCRIPTION OF THE PREFERRED EMBODIMENTS

Figure 1:
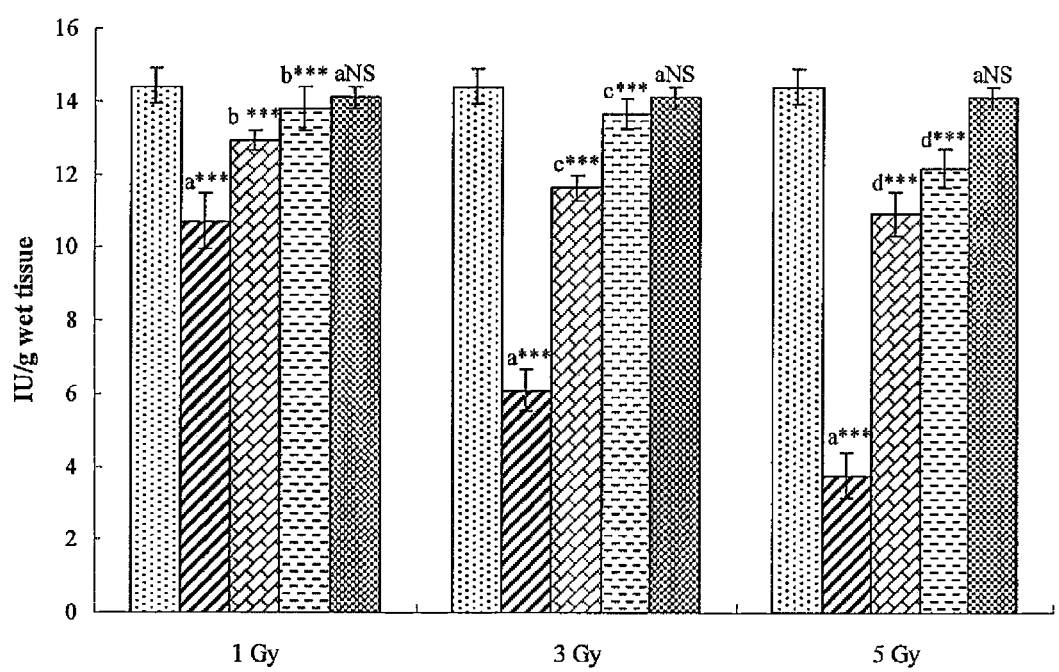
Figure 2:
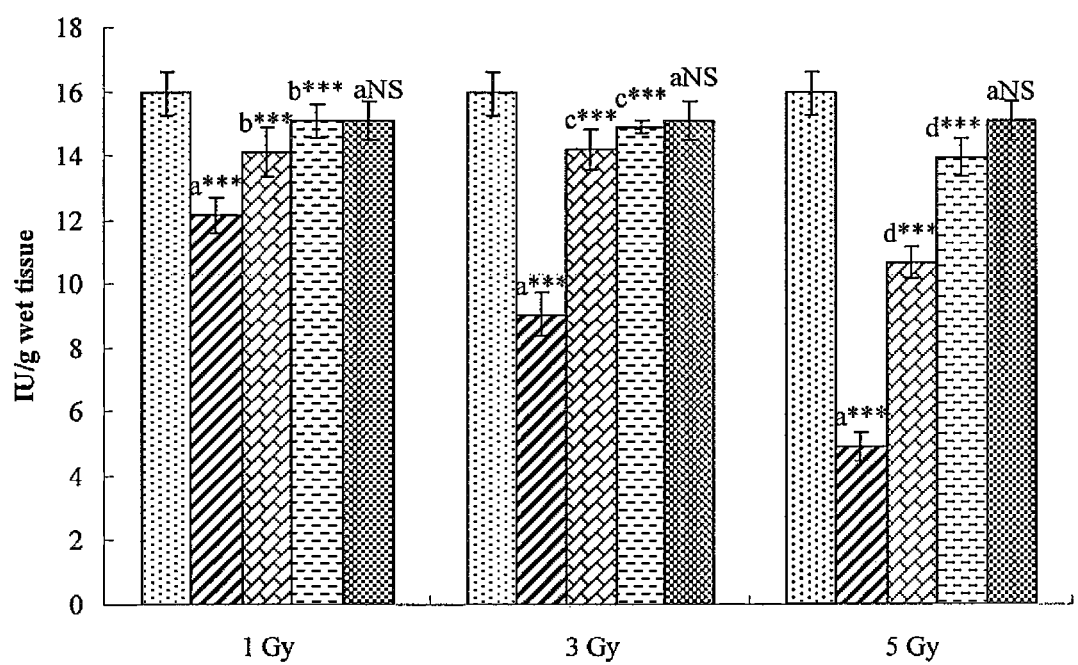
FIG. 2 is a graph showing changes in the hepatic alanine transaminase (ALT) level of rats treated with hesperidin after exposure to various doses of gamma radiation in accordance with an embodiment of the present invention.
Figure 3:
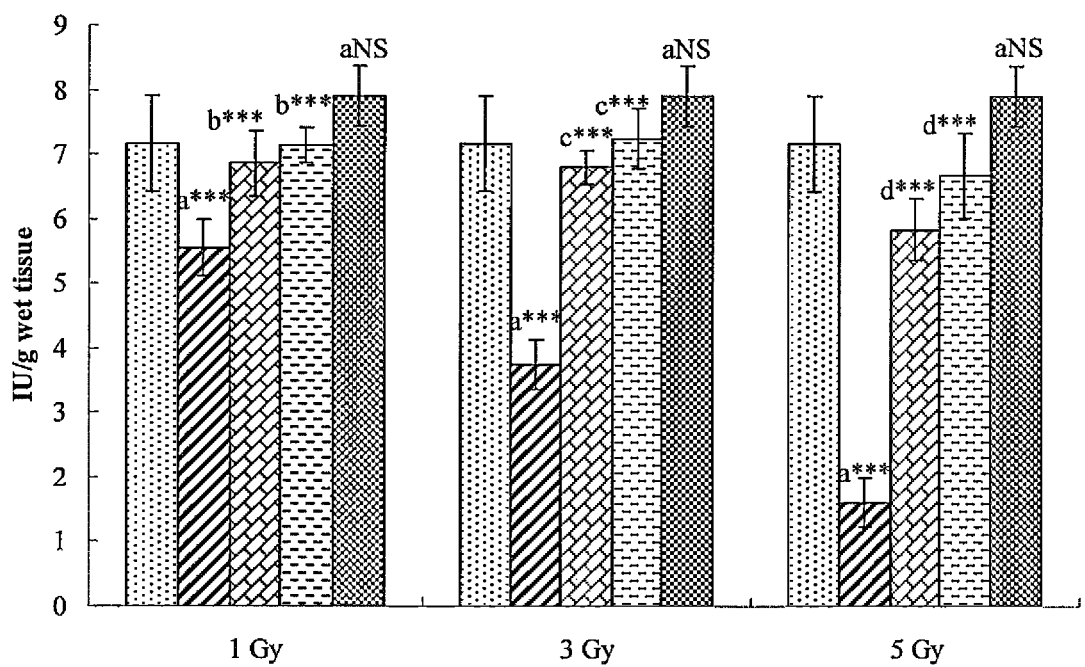
FIG. 3 is a graph showing changes in the hepatic alkaline phosphatase (ALP) level of rats treated with hesperidin after exposure to various doses of gamma radiation in accordance with an embodiment of the present invention.
Figure 4:
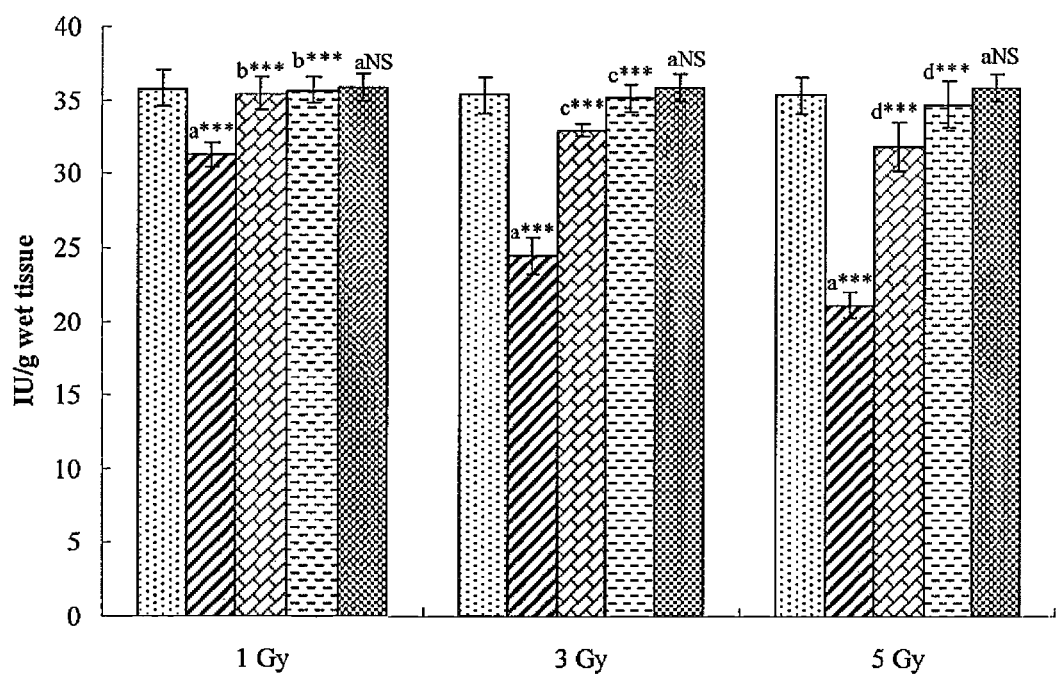
FIG. 4 is a graph showing changes in the hepatic lactate dehydrogenase (LDH) level of the rats treated with hesperidin after exposure to various doses of gamma radiation in accordance with an embodiment of the present invention.
Figure 5:
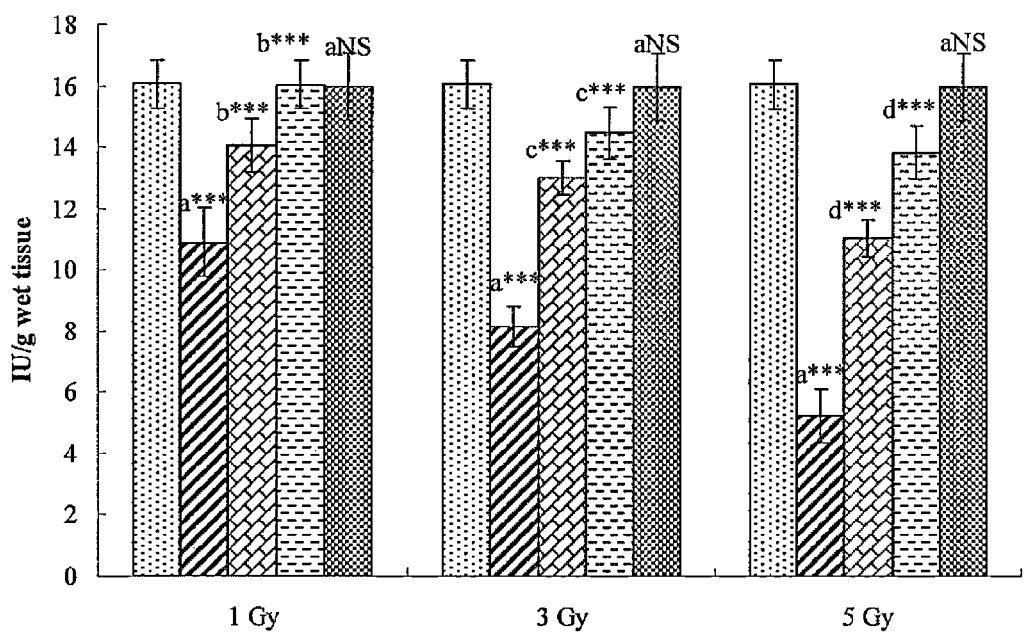
FIG. 5 is a graph showing changes in the hepatic gamma-glutamyl transpeptidase (γ-GT) level of rats treated with hesperidin after exposure to various doses of gamma radiation in accordance with an embodiment of the present invention.

In accordance with a first aspect thereof, the present invention pertains to a cytoprotective composition comprising hesperidin, represented by the following chemical formula 1, or a pharmaceutically acceptable salt thereof as an active ingredient.

[Chemical Formula 1]

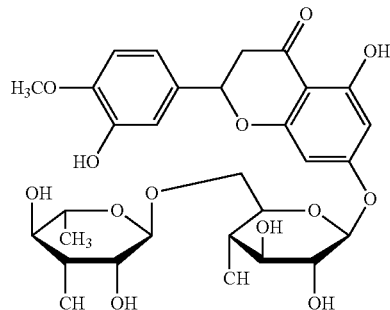

In an embodiment of the first aspect of the present invention, the cytoprotective composition comprising hesperidin or a pharmaceutically acceptable salt thereof as an active ingredient is protective against radiation-induced cell damage.

In another embodiment of the first aspect of the present invention, the cytoprotective composition comprising hesperidin or a pharmaceutically acceptable salt thereof as an active ingredient is protective against cell damage caused by X rays, α radiation, β radiation, or γ radiation.

In a further embodiment of the first aspect of the present invention, the cytoprotective composition comprising hesperidin or a pharmaceutically acceptable salt thereof as an active ingredient is protective against γ radiation-induced cell damage.

In still a further embodiment of the first aspect of the present invention, the cytoprotective composition comprising hesperidin or a pharmaceutically acceptable salt thereof as an active ingredient is protective against radiation-induced hepatic damage.

In still another embodiment of the first aspect of the present invention, the cytoprotective composition comprising hesperidin or a pharmaceutically acceptable salt thereof as an active ingredient is useful in the restoration of decreased body weights, liver weights, and spleen indices after exposure to radiation.

In still a further embodiment of the first aspect of the present invention, the cytoprotective composition comprising hesperidin or a pharmaceutically acceptable salt thereof as an active ingredient is useful in the restoration to normal levels of the increased activity of serum marker enzymes following exposure to radiation.

In yet another embodiment of the first aspect of the present invention, the cytoprotective composition comprising hesperidin or a pharmaceutically acceptable salt thereof as an active ingredient is useful in the restoration to normal levels of the decreased activity of hepatic marker enzymes after exposure to radiation.

In yet a further embodiment of the first aspect of the present invention, the cytoprotective composition comprising hesperidin or pharmaceutically acceptable salts thereof as an active ingredient is useful in the restoration to normal of the radiation-induced decreased or increased activity of marker enzymes including aspartate transaminase (AST), alanine transaminase (ALT), alkaline phosphatase (ALP), lactate dehydrogenase (LDH), and gamma-glutamyl transpeptidase (γ-GT), after exposure to radiation.

In yet a further embodiment of the first aspect of the present invention, the cytoprotective composition comprising hesperidin or a pharmaceutically acceptable salt thereof as an active ingredient is useful in the restoration to normal states of a radiation-induced increased hepatic lipid peroxidation activity after exposure to radiation.

In yet another embodiment of the first aspect of the present invention, the cytoprotective composition comprising hesperidin or a pharmaceutically acceptable salt thereof as an active ingredient is useful in the restoration to normal states of the radiation-induced decreased activity of, enzymatic anti-oxidants, such as superoxide dismutase (SOD) or glutathione peroxidase (GPx), within the liver after exposure to radiation.

In yet a further embodiment of the first aspect of the present invention, the cytoprotective composition comprising hesperidin or a pharmaceutically acceptable salt thereof as an active ingredient is useful in the restoration to normal states of the radiation-induced decreased activity of non-enzymatic antioxidants, such as glutathione, vitamin C and vitamin E, within the liver following exposure to radiation.

In accordance with a second aspect thereof, the present invention pertains to a cytoprotective health food composition comprising hesperidin or a pharmaceutically acceptable salt thereof as an active ingredient.

In accordance with a third aspect thereof, the present invention pertains to a method for protecting normal cells of a subject undergoing radiation therapy, comprising administering hesperidin or a pharmaceutically acceptable salt thereof in a therapeutically effective amount to the subject.

In an embodiment of the third aspect of the present invention, the method for protecting normal cells of a subject under radiation therapy, comprising administering hesperidin or a pharmaceutically acceptable salt thereof in a therapeutically effective amount to the subject is applicable for protection against cell damage caused by X rays, α radiation, β radiation, or γ radiation.

In another embodiment of the third aspect of the present invention, the method for protecting normal cells of a subject undergoing radiation therapy, comprising administering hesperidin or a pharmaceutically acceptable salt thereof in a therapeutically effective amount to the subject is applicable for protection against γ radiation-induced cell damage.

In a further embodiment of a third aspect of the present invention, the method for protecting normal cells of a subject undergoing radiation therapy, comprising administering hesperidin or a pharmaceutically acceptable salt thereof in a therapeutically effective amount to the subject is applicable for protection against radiation-induced hepatocytic damage.

In still another embodiment of a third aspect of the present invention, the method for protecting normal cells of a subject undergoing radiation therapy, comprising administering hesperidin or a pharmaceutically acceptable salt thereof in a therapeutically effective amount to the subject is applicable for the restoration of decreased body weights, liver weights, and spleen indices after exposure to radiation.

In still a further embodiment of the third aspect of the present invention, the method for protecting normal cells of a subject undergoing radiation therapy, comprising administering hesperidin or a pharmaceutically acceptable salt thereof in a therapeutically effective amount to the subject is applicable for the restoration to normal states of the radiation-induced increased activity of serum marker enzymes following exposure to radiation.

In yet another embodiment of the third aspect of the present invention, the method for protecting normal cells of a subject undergoing radiation therapy, comprising administering hesperidin or a pharmaceutically acceptable salt thereof in a therapeutically effective amount to the subject is applicable for restoration to normal states of the radiation-induced decreased activity of hepatic marker enzymes following exposure to radiation.

In yet a further embodiment of the third aspect of the present invention, the method for protecting normal cells of a subject undergoing radiation therapy, comprising administering hesperidin or a pharmaceutically acceptable salt thereof in a therapeutically effective amount to the subject is applicable for the restoration to normal states of the radiation-induced decreased or increased activity of, marker enzymes including aspartate transaminase (AST), alanine transaminase (ALT), alkaline phosphatase (ALP), lactate dehydrogenase (LDH), and gamma-glutamyl transpeptidase (γ-GT) after exposure to radiation.

In yet still a further embodiment of the third aspect of the present invention, the method for protecting normal cells of a subject undergoing radiation therapy, comprising administering hesperidin or a pharmaceutically acceptable salt thereof in a therapeutically effective amount to the subject is applicable for the restoration to normal of increased hepatic lipid peroxidation following exposure to radiation.

In yet still another embodiment of the third aspect of the present invention, the method for protecting normal cells of a subject undergoing radiation therapy, comprising administering hesperidin or a pharmaceutically acceptable salt thereof in a therapeutically effective amount to the subject is applicable for the restoration to normal of the radiation-induced decreased activity of enzymatic anti-oxidants, such as superoxide dismutase (SOD) or glutathione peroxidase (GPx), within the liver after exposure to radiation.

In yet a further embodiment of the third aspect of the present invention, the method for protecting normal cells of a subject undergoing radiation therapy, comprising administering hesperidin or a pharmaceutically acceptable salt thereof in a therapeutically effective amount to the subject is applicable for the restoration to normal of the radiation-induced decreased activity of non-enzymatic antioxidants, such as glutathione, vitamin C and vitamin E, within the liver after exposure to radiation.

Hesperidin has a molecular formula of $C_{28}H_{34}O_{15}$ with a molecular weight of 610 and is in the form of a flavanone glycoside (glucoside) comprised of the flavanone hesperitin and the disaccharide rutinose. Citrus fruits such as lemons and oranges, particularly the unripe fruits, are abundant in hesperidin. The peel and membranous parts of these fruits have the highest hesperidin concentrations which amount to 1.5~3%. This flavonoid is found in green vegetables, as well. The hesperidin useful in the present invention may be one extracted from citrus fruits using a method known in the art or synthesized using a method known in the art, or a commercially available one. Citrus fruits abundant in hesperidin may be exemplified by mandarins, *Citrus grandis*, oranges, lemons, tangerines, pomelo, and citrons. With regard to the preparation of extracts from the peels of citrus fruits, reference may be made to literature such as the Merck Index, and patents.

It should be understood that in addition to hesperidin itself and pharmaceutically acceptable salts thereof, solvates and hydrates that can be prepared therefrom are included within the scope of the present invention.

Hesperidin may be used in the form of pharmaceutically acceptable salts in accordance with the present invention. Within the range of these salts are included acid addition salts formed with pharmaceutically acceptable free acids. Useful as the free acids are inorganic acids such as hydrochloric acid, nitric acid, phosphoric acid, sulfuric acid, hydrobromic acid, hydroiodic acid, nitrous acid, and phosphorous acid, and non-toxic organic acids such as aliphatic mono- and dicarboxylate, phenyl-substituted alkanoate, hydroxy alkanoate and alkanedioate, aromatic acids, aliphatic and aromatic sulfonic acids. Examples of such non-toxic bases include sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprilate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylene benzoate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate and mandelate.

The acid addition salts of hesperidin according to the present invention may be prepared using a conventional method, for example, by dissolving hesperidin in excess acid in water and precipitating the resulting salt in a water-miscible organic solvent, e.g., methanol, ethanol, acetone or acetonitrile.

Alternatively, hesperidin may be heated along with one volume of acid or alcohol in water, followed by evaporating the mixture and drying or suction filtering the precipitate to prepare acid addition salts thereof.

Also, metal salts formed with bases may fall within the range of pharmaceutically acceptable salts of the compounds of the present invention. Examples of the metal salts useful in the present invention include alkali metal salts and alkaline earth metal salts. For example, the compound of the present invention may be dissolved in excess alkali metal hydroxide or alkaline earth metal hydroxide in water, and after the removal of non-dissolved compound salts through filtration, the filtrate thus obtained may be dried to afford the pharmaceutically acceptable salts of the compound of the present invention. Suitable for use in pharmaceutics are sodium, potassium or calcium salts. Corresponding silver salts may be obtained by reacting the alkali metal or alkaline earth metal salts with suitable silver salt (e.g., silver nitrate).

Hesperidin or pharmaceutically acceptable salts thereof in accordance with the present invention protect cells from being injured by X rays, α, β or γ radiation and preferably γ radiation. In detail, experiments with rats exposed to radiation showed that hesperidin had restorative effects on a radiation-induced decrease in body weight, liver weight and spleen index (refer to Table 1), a radiation-induced increase in the activity of serum marker enzymes, a radiation-induced decrease in the activity of hepatic marker enzymes (refer to Tables 2 and 3, and FIGS. 1 to 5), a radiation-induced increase in lipid peroxidation within the liver (refer to Table 4 and FIG. 6), and a radiation-induced decrease in the activity of hepatic enzymatic antioxidants such as superoxide dismutase (SOD) and glutathione peroxidase (GPx) and in the activity of non-enzymatic antioxidants such as glutathione, vitamin C and vitamin E.

Preferable examples of the marker enzymes include aspartate transaminase (ALT), alkaline phosphatase (ALP), lactate dehydrogenase (LDH) and γ-glutamyl transpeptidase (γ-GT).

Additionally, the liver tissues administered with hesperidin in isolation were found to undergo neither necrosis or apoptosis, and show hepatocytes without injury in the centrilobular regions, and normal liver plates and epithelial cells (Tables 1~4, FIGS. 1~10). Almost none of the cellular parameters measured after administration with hesperidin alone were changed, indicating that hesperidin is not toxic to cells.

Therefore, hesperidin protects cells against radiation such as gamma radiation and is safe to cells so that it can be used as an effective cytoprotective against radiation.

A composition comprising hesperidin or a pharmaceutically acceptable salt thereof as an active ingredient in accordance with the present invention may be in the form of a general drug agent. That is, hesperidin or pharmaceutically acceptable salts thereof may be administered as various oral or non-oral dosage forms for clinical practice.

In addition to the active ingredient, the pharmaceutical composition in accordance with the present invention may include at least one pharmaceutically acceptable carrier. Examples of the pharmaceutically acceptable carrier include saline, sterile water, Ringer's solution, buffered saline solution, dextrose solution, maltodextrin solution, glycerol, ethanol, and a mixture of two or more thereof. If necessary, the composition may further include other conventional additives, such as antioxidants, buffers, and bacteriostatic agents.

Solid preparations intended for oral administration of the compound of the present invention may take the form of tablets, pills, powders, granules, capsules, and the like. In regards to these solid agents, hesperidin is formulated in combination with at least one excipient such as starch, calcium carbonate, sucrose, lactose, or gelatin. In addition, a lubricant such as magnesium stearate, talc, or the like may also be added.

Liquid preparations intended for oral administration include suspensions, internal use solutions, emulsion, syrups, and the like. In addition to a simple diluent such as water or liquid paraffin, various excipients, such as wetting agents, sweetening agents, aromatics, preservatives, and the like may be contained in the liquid preparations. Also, the compound of the present invention may be administered via a non-oral route. For this, sterile aqueous solutions, non-aqueous solvents, suspensions, emulsions, lyophilizates, suppositories, and the like may be used. Injectable propylene glycol, polyethylene glycol, vegetable oils such as olive oil, and esters such as ethyl oleate may be suitable for non-aqueous solvents and suspensions. The basic materials of suppositories include Witepsol, macrogol, Tween 61, cacao butter, laurin butter, glycerol, and glycerogelatin.

According to purposes, the pharmaceutical composition of the present invention may be administered non-orally, that is, subcutaneously, intravenously, or intramuscularly. For non-oral dosage preparations, hesperidin may be mixed with a stabilizer or buffer in water and the resulting solution or suspension may be packaged into unit dosage forms, such as ampules or vials.

The effective dosage of the active ingredient in accordance with the present invention depends on various factors, including the patient's weight, age, gender, state of health, diet, the time of administration, route of administration, excretion rate, severity of disease, etc. The active ingredient according to the present invention may be administered in a single dose or in multiple doses per day at a daily dose ranging from 250 to 3,000 mg for adults.

Also provided is a health food composition for protecting cells against radiation, comprising hesperidin and a food additive.

With the aim of protecting cells from radiation, hesperidin or the pharmaceutically acceptable salts thereof may be added to health food. As a food additive, hesperidin may be properly used alone or in combination with other food ingredients according to a conventional method. The amount of the active ingredient according to the present invention may vary depending on the purpose thereof (prevention, health improvement or therapeutic treatment). Generally, when used for the preparation of foods or beverages, the active ingredient according to the present invention may be added in an amount of 1 to 20 weight % based on the total weight of the health food and preferably in an amount of 5 to 10 weight %. In the case where the active ingredient is applied to health foods which are designed to be taken habitually, its content may be below the above-mentioned range. However, hesperidin does not have the problem of being harmful to the body and thus can be used in an amount exceeding the ranges specified.

No particular limitations are imposed on the kind of foods to which the active ingredient, e.g., hesperidin or the pharmaceutically acceptable salts thereof can be added. Examples of such foods include beverages, gum, vitamin complexes, and healthy food supplementals and are not limited thereto. All usually accepted health foods may contain the active ingredient according to the present invention.

A healthy beverage composition according to the present invention may further contain various fragrant or natural carbohydrates. Examples of such natural carbohydrates include monosaccharides, such as glucose and fructose, disaccharides such as maltose and sucrose, polysaccharides such as dextrin and cyclodextrin, and sugar alcohols such as xylitol, sorbitol and erythritol. Also, sweeteners, e.g., natural sweeteners such as thaumatin and a stevia extract, or synthetic sweeteners such as saccharin and aspartame, may be added to the health food to which the active ingredient of the present invention is applied. The natural carbohydrate may be used in an amount of approximately 0.01~0.04 grams based on 100 mL of the beverage composition of the present invention, and preferably in an amount of approximately 0.02~0.03 grams.

In addition, the health food composition of the present invention may contain various nutrients, vitamins, minerals, electrolytes, flavors, colorants, pectic acid and salts thereof, alginic acid and salts thereof, organic acids, protective colloidal thickeners, pH modifiers, stabilizers, antiseptics, glycerin, alcohols, and carbonating agents used in carbonated beverages. Moreover, the composition of the present invention can contain fruit flesh for preparing natural fruit juices, fruit beverages and vegetable beverages. These ingredients may be used individually or in combination. The ratio of these additives is not important, but is generally selected in a range of 0.01 to 0.1 weight parts per 100 weight parts of the composition of the present invention.

A better understanding of the present invention may be obtained through the following examples which are set forth for purposes of illustration, but are not to be construed as to limit the present invention.

EXAMPLE 1

Cytoprotective Activity of Hesperidin Against Radiation-Induced Injury

An assay of hesperidin in accordance with the present invention was performed for cytoprotective activity against radiation-induced cell injury.

SD female rats, each weighing 150±5 g, were purchased from Central Lab. Animal Inc., Seoul, Korea, and bred in an animal lab set at a temperature of 23±2° C. and RE 55±10% under a light condition of 12L/12D. The rats were divided into 11 groups of six which were treated as follows:

(1) Group 1: control supplied with saline for 7 days
(2) Group 2: after irradiation with γ radiation at a dose of 1 Gy, were allowed to stand for 7 days
(3) Group 3: after irradiation with γ radiation at a dose of 1 Gy, were administered hesperidin orally at a dose of 50 mg/kg for 7 days
(4) Group 4: after irradiation with γ radiation at a dose of 1 Gy, were administered hesperidin orally at a dose of 100 mg/kg for 7 days
(5) Group 5: after irradiation with γ radiation at a dose of 3 Gy, were allowed to stand for 7 days
(6) Group 6: after irradiation with γ radiation at a dose of 3 Gy, were administered hesperidin at a dose of 50 mg/kg for 7 days
(7) Group 7: after irradiation with γ radiation at a dose of 3 Gy, were administered hesperidin at a dose of 100 mg/kg for 7 days
(8) Group 8: after irradiation with γ radiation at a dose of 5 Gy, were allowed to stand for 7 days
(9) Group 9: after irradiation with γ radiation at a dose of 5 Gy, were administered hesperidin at a dose of 50 mg/kg for 7 days
(10) Group 10: after irradiation with γ radiation at a dose of 5 Gy, were administered hesperidin at a dose of 100 mg/kg for 7 days
(11) Group 11: administered hesperidin at a dose of 100 mg/kg for 7 days 24 hours after the final administration of hesperidin, blood samples were withdrawn from the retro-orbital plexus vein of the rats under ether anesthesia. The blood samples were centrifuged at 3,000 rpm for 20 min to separate sera which were then stored at 4° C. until use. After being sacrificed, the rats were splenectomized and hepatectomized. The spleens and the livers thus obtained were washed with cold saline and dried before weighing. The liver tissue was homogenized to a 10% homogenate suspension in phosphate buffered saline (0.1 M, pH 7.4) using a Wisestir™ HS 30E homogenizer. After the centrifugation of the crude homogenate at 1,500 rpm at 4° C. for 10 min, the supernatant was used for biochemical analysis. The liver tissue was also fixed in 10% formalin for histopathological analysis.

Aspartate transaminase (AST) and alanine transaminase (ALT) in the sera and the liver tissue homogenate suspension were assayed according to the methods of Bergmeyer et al. [Bergmeyer, H. U., Scheibe, P., Wahlefeld, A. W., 1978. Optimization of methods for aspartate aminotransferase and alanine aminotransferase. Clin. Chem. 24, 58-61]. As for alkaline phosphatase (ALP) in the sera and the liver tissue homogenate suspension, its activity was assayed by the method of King [King, J., 1965a. The phosphohydrolases-acid and alkaline phosphatases. In: Practical Clinical Enzymology. Van Nostrand, D., Co Ltd., London, pp. 191-208] with disodium phenylphosphate as substrate. Lactate dehydrogenase (LDH) was also analyzed for activity by the method of King [King, J., 1965a. The phosphohydrolases-acid and alkaline phosphatases. In: Practical Clinical Enzymology. Van Nostrand, D., Co Ltd., London, pp. 191-208] with lithium lactate as a substrate. The activity of gamma glutamyl transpeptidase (γ-GT) was determined according to the method of Rosalki and Rau [Rosalki, S. B., Rau, D., 1972. Serum-glutamyl transpeptidase activity in alcoholism. Clin Chim Acta. 39, 41-47] with L-γ-glutamyl-p-nitroanilide. Proteins were quantified according to the Bradford assay [Bradford, M. M., 1976. A rapid and sensitive method for the quantitation of microgram quantities of protein utilizing the principle of protein-dye binding. Anal Biochem. 72, 248-254] using bovine serum albumin as a protein standard. Serum ceruloplasmin levels were determined by the method of Curzon and Vallet [Curzon, G., Vallet, L., 1960. The purification of human ceruloplasmin. *Biochem J.* 74, 279-287]

with N,N-dimethyl-p-phenylenediamine monohydrochloride as a substrate. Hepatic lipid peroxidation was measured by the method of Ohkawa et al. [Ohkawa, H., Ohishi, N., Yagi, K., 1979. Assay for lipid peroxides in animal tissues by thiobarbituric acid reaction. Anal. Biochem. 95, 351-358]. For the analysis of superoxide dismutase (SOD) and catalase, a commercially available kit (Calbiochem, Germany) was used. An assay was made of glutathione peroxidase (GPx) by the method of Rotruck et al. [Rotruck, J. T., Pope, A. L., Ganther, H. E., Swanson, A. B., Hafeman, D. G., Hoekstra, W. G., 1973. Selenium: biochemical role as a component of glutathione peroxidase. Science 179, 588-590] and of reduced glutathione (GSH) content by the method of Beutler et al. [Beutler, E., Duron, O., Kelly, B. M., 1963. Improved method for the determination of blood glutathione. J. Lab. Clin. Med. 61, 882-888]. Vitamins C and E were measured according to the methods of Omaye et al. [Omaye, S. T., Turnbull, J. D., Sauberlich, H. E., 1979. Selected methods for the determination of ascorbic acid in animal cells, tissues and fluids. Methods Enzymol. 62, 1-11] and Kayden et al. [Kayden, H. J., Chow, C. K., Bjornson, L. K., 1973. Spectrophotometric method for determination of tocopherol in red blood cells. J Lipid Res 14, 533-540], respectively. For histopathological analysis, the liver tissues were washed sequentially with ethanol and xylene in that order and embedded in paraffin wax, followed by sectioning into 5 microslides using a microtome (Leica Microsystems, Germany). These sections were deparaffinized, stained with hematoxylin and eosin and photographed under a microscope (Nikon Eclipse E 400). Splenic index was calculated according to the following mathematical formula 1.

$$\frac{\text{Spleen Weight}}{\text{Body Weight}} \times 100 \quad [\text{Mathematical Formula 1}]$$

Statistical differences were determined using a one-way ANOVA followed by Tukey's multiple comparison test. Values for each group of six rats represent mean ±S.D. Differences were considered significant if the P value was <0.05.

A. Effect of Hesperidin on Body Weight, Liver Weight and Splenic Index

Measurements of body weights, liver weights and splenic indices for each group are summarized in Table 1, below.

TABLE 1

| Group Nos. | Body Wt. (g) | Liver Wt. (g) | Splenic Indices |
|---|---|---|---|
| 1 | 155.51 ± 4.02 | 5.62 ± 0.54 | 0.358 ± 0.013 |
| 2 | 149.76 ± 1.05 a*** | 4.70 ± 0.14 a*** | 0.291 ± 0.032 a*** |
| 3 | 155.06 ± 3.79 b*** | 5.13 ± 0.19 b*** | 0.352 ± 0.014 b*** |
| 4 | 155.65 ± 1.15 b*** | 5.26 ± 0.13 b*** | 0.348 ± 0.012 b*** |
| 5 | 146.85 ± 1.06 a*** | 3.96 ± 0.14 a*** | 0.220 ± 0.012 a*** |
| 6 | 151.53 ± 1.11 c*** | 4.51 ± 0.14 c*** | 0.326 ± 0.013 c*** |
| 7 | 152.40 ± 1.44 c*** | 4.89 ± 0.18 c*** | 0.341 ± 0.008 c*** |
| 8 | 142.63 ± 1.85 a*** | 3.82 ± 0.20 a*** | 0.150 ± 0.007 a*** |
| 9 | 148.87 ± 1.06 d*** | 4.34 ± 0.13 d*** | 0.261 ± 0.012 d*** |
| 10 | 150.99 ± 1.61 d*** | 4.84 ± 0.08 d*** | 0.349 ± 0.009 d*** |
| 11 | 154.24 ± 1.14 aNS | 5.28 ± 0.11 aNS | 0.354 ± 0.004 aNS | a: compared to Group 1
b: compared to Group 2
c: compared to Group 5
d: compared to Group 8
***P < 0.001

As understood from the data of Table 1, rats decreased in body weight, liver weight and splenic index when irradiated with gamma radiation (Groups 2, 5 and 8), but administration with hesperidin restored the decreased values to near normal ones (control) (Groups 3, 4, 6, 7, 9 and 10).

B. Effect of Hesperidin on Serum Marker Enzymes in Hepatocytes

After the experiments, each group was assayed for the activity of serum marker enzymes (AST, ALT, ALP, LDH, γ-GT and ceruloplasmin) and the results are given in Tables 2 and 3, below.

TABLE 2

| Group Nos. | AST | ALT | ALP |
|---|---|---|---|
| 1 | 41.79 ± 2.26 | 43.70 ± 1.16 | 93.53 ± 2.45 |
| 2 | 60.30 ± 1.28 a*** | 52.00 ± 1.58 a*** | 114.98 ± 3.69 a*** |
| 3 | 45.95 ± 1.09 b*** | 46.08 ± 1.04 b*** | 97.76 ± 1.93 b*** |
| 4 | 42.60 ± 1.77 b*** | 43.36 ± 1.18 b*** | 95.85 ± 3.61 b*** |
| 5 | 69.10 ± 1.89 a*** | 63.27 ± 1.90 a*** | 140.59 ± 2.84 a*** |
| 6 | 48.32 ± 1.66 c*** | 51.02 ± 1.14 c*** | 111.04 ± 2.38 c*** |
| 7 | 46.02 ± 1.24 c*** | 45.83 ± 1.04 c*** | 99.88 ± 3.49 c*** |
| 8 | 78.68 ± 4.40 a*** | 72.73 ± 2.08 a*** | 155.47 ± 3.97 a*** |
| 9 | 53.78 ± 2.69 d*** | 56.50 ± 4.03 d*** | 112.90 ± 6.80 d*** |
| 10 | 50.29 ± 1.12 d*** | 48.26 ± 2.17 d*** | 99.63 ± 4.12 d*** |
| 11 | 41.38 ± 1.74 aNS | 43.73 ± 1.30 aNS | 91.38 ± 1.92 aNS | a: compared to Group 1
b: compared to Group 2
c: compared to Group 5
d: compared to Group 8
***P < 0.001

TABLE 3

| Group Nos. | LDH | γ-GT | Ceruloplasmin |
|---|---|---|---|
| 1 | 142.99 ± 2.42 | 91.77 ± 1.84 | 20.72 ± 1.05 |
| 2 | 153.59 ± 2.87 a*** | 113.49 ± 2.41 a*** | 17.52 ± 0.86 a*** |
| 3 | 145.16 ± 3.61 b*** | 96.35 ± 2.10 b*** | 19.75 ± 0.53 b*** |
| 4 | 143.14 ± 2.63 b*** | 91.33 ± 1.10 b*** | 19.73 ± 1.08 b*** |
| 5 | 176.02 ± 2.70 a*** | 144.39 ± 2.70 a*** | 13.39 ± 1.84 a*** |
| 6 | 148.47 ± 1.58 c*** | 116.29 ± 1.76 c*** | 18.34 ± 1.49 c*** |
| 7 | 144.38 ± 1.22 c*** | 98.47 ± 2.29 c*** | 20.56 ± 1.14 c*** |
| 8 | 216.38 ± 3.81 a*** | 171.25 ± 2.16 a*** | 11.70 ± 1.26 a*** |
| 9 | 159.73 ± 4.19 d*** | 120.05 ± 8.37 d*** | 17.23 ± 1.31 d*** |
| 10 | 151.66 ± 2.15 d*** | 108.47 ± 2.94 d*** | 18.74 ± 0.55 d*** |
| 11 | 142.83 ± 2.05 aNS | 91.11 ± 1.47 aNS | 20.54 ± 0.81 aNS | a: compared to Group 1
b: compared to Group 2
c: compared to Group 5
d: compared to Group 8
***P < 0.001

As seen in Tables 2 and 3, rats, when exposed to gamma radiation, showed sharp increases in the activity of serum marker enzymes (AST, ALT, ALP, LDH, γ-GT and ceruloplasmin) (Groups 2, 5 and 8) in comparison with the control (Group 1), but the activity was restored to near normal (control) after administration with hesperidin for 7 days (Groups 3, 4, 6, 7, 9 and 10).

Thus, hesperidin significantly suppresses gamma radiation-induced increase in the activity of serum marker enzymes and thus prevents damage to cells, leading to cell protection.

More than 100 mg/kg of hesperidin is needed for cytoprotective activity upon irradiation with gamma radiation at a dose of 5 Gy while only 50 mg/kg of hesperidin can protect cells against 1 Gy or 3 Gy of gamma radiation.

Showing significant cytoprotective effects on cells exposed to radiation, hesperidin in accordance with the present invention is useful in the suppression of the side effects of radiotherapy.

C. Effect of Hesperidin on Tissue Marker Enzymes in Hepatocytes

After the experiments, each group was assayed for the activity of tissue marker enzymes (AST, ALT, ALP, LDH and γ-GT) and the results are shown in FIGS. 1 to 5.

As depicted in FIGS. 1 to 5, the rats exposed to gamma radiation (Groups 2, 5 and 8) decreased in the activity of hepatic tissue marker enzymes (AST, ALT, ALP, LDH and γ-GT) in comparison with the control (Group 1), but hesperidin restored the decreased activity to near normal (control) after the administration of hesperidin for 7 days (Groups 3, 4, 6, 7, 9 and 10).

Hence, hesperidin is protective of cells as it significantly suppresses gamma radiation-induced reduction in the activity of tissue marker enzymes, thereby showing that it checks cell damage.

D. Effect of Hesperidin on Lipid Peroxidation in Liver Tissue

Figure 6:
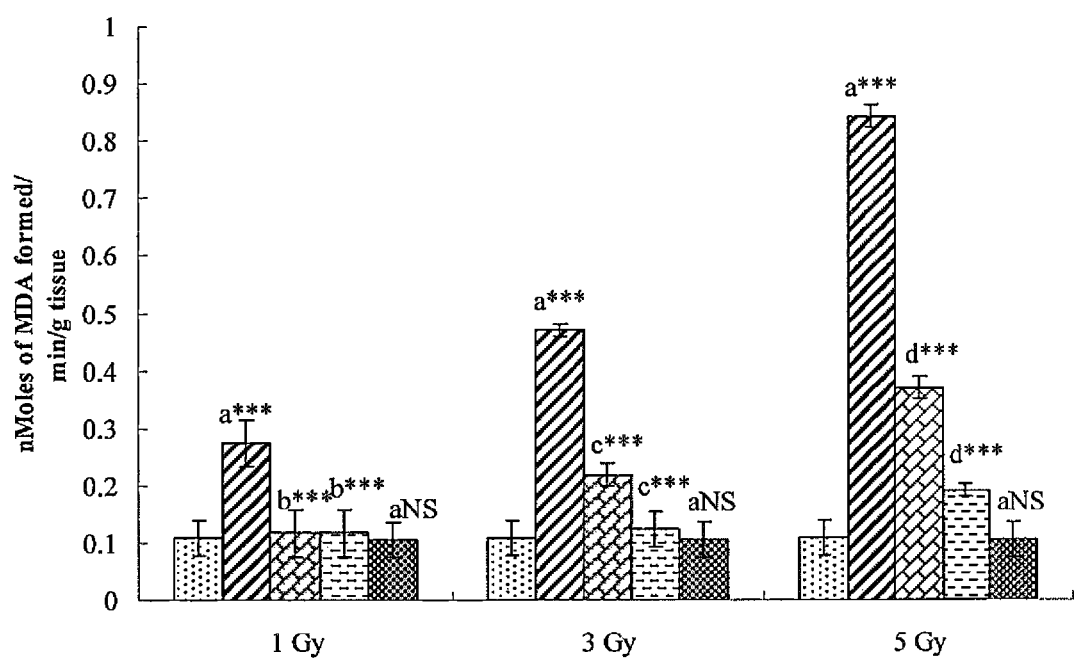
FIG. 6 is a graph showing changes in the hepatic lipid peroxidation activity of rats treated with hesperidin after exposure to various doses of gamma radiation in accordance with an embodiment of the present invention.

Lipid peroxidation was detected in the liver specimens of rats with TBARS (thiobarbituric acid-reacting substances) assay, and the results are depicted in FIG. 6.

As seen in FIG. 6, rats irradiated with gamma radiation sharply increased in TBARS level in comparison with the control, but were restored to a near normal state (control) after administration with hesperidin for 7 days. In rats exposed to radiation doses of 1 Gy, 3 Gy and 5 Gy, hesperidin showed protective rates of 94.5%, 69.61% and 64.53%, respectively, when administered at a dose of 50 mg/kg and 97.59%, 95.8% and 88.7%, respectively, when administered at a dose of 100 mg/kg.

These results suggest that hesperidin significantly prevents cell damage by suppressing gamma radiation-induced increases in hepatic lipid peroxidation, resulting in a conclusion of cytoprotection.

E. Effect of Hesperidin on Enzymatic Antioxidants in Liver Tissue

Figure 7:
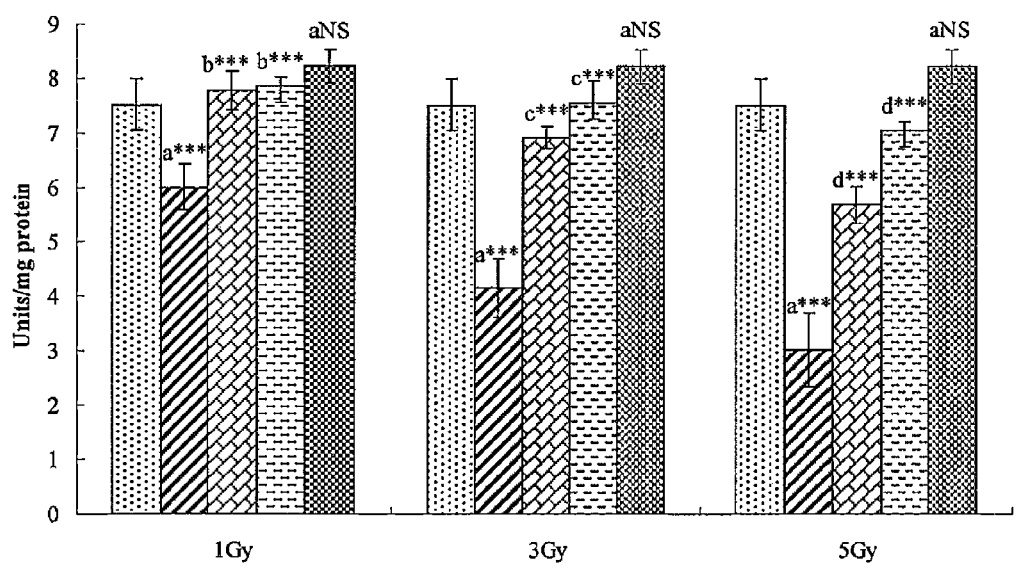
FIG. 7 is a graph showing changes in the superoxide dismutase (SOD) level of rats treated with hesperidin after exposure to various doses of gamma radiation in accordance with an embodiment of the present invention.
Figure 8:
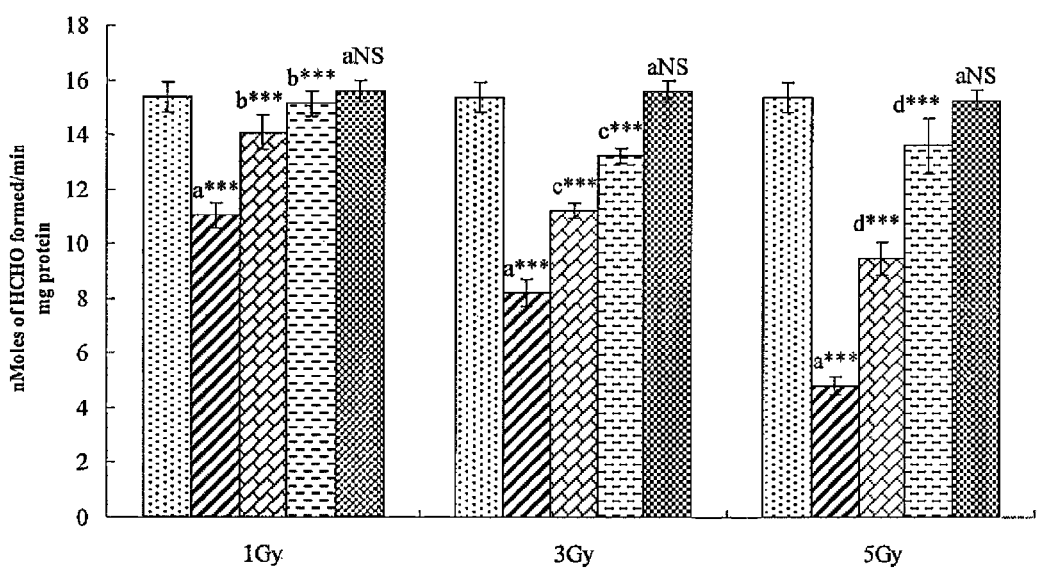
FIG. 8 is a graph showing changes in the hepatic catalase level of rats treated with hesperidin after exposure to various doses of gamma radiation in accordance with an embodiment of the present invention.
Figure 9:
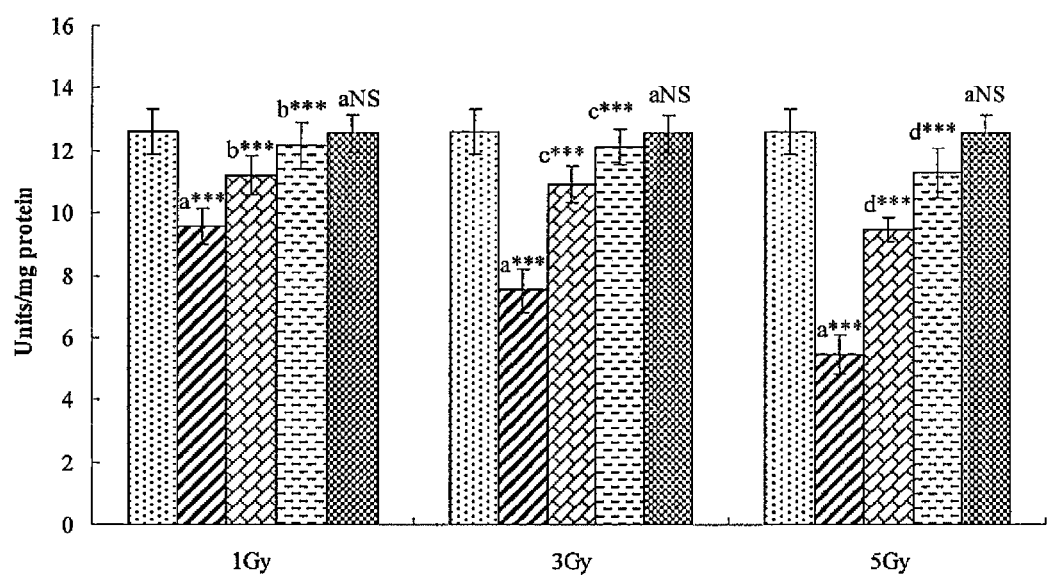
FIG. 9 is a graph showing changes in the hepatic glutathione peroxidase (GPx) level of rats treated with hesperidin after exposure to various doses of gamma radiation in accordance with an embodiment of the present invention.

After the experiments, each group was assayed for the activity of enzymatic antioxidants (SOD, catalase and GPx) and the results are shown in FIGS. 7 to 9.

As illustrated in FIGS. 7 to 9, the rats exposed to gamma radiation (Groups 2, 5 and 8) significantly decreased in the activity of hepatic enzymatic antioxidants (SOD, catalase and GPx) in comparison with the control (Group 1), but hesperidin restored the decreased activity to near normal (control) after administration for 7 days (Groups 3, 4, 6, 7, 9 and 10).

These results suggest that hesperidin significantly prevents cell damage by suppressing gamma radiation-induced decreases in the activity of hepatic enzymatic antioxidants, resulting in a conclusion of cytoprotection.

F. Effect of Hesperidin on Non-Enzymatic Antioxidants in Liver Tissue

After the experiments, each group was assayed for the activity of hepatic non-enzymatic antioxidants (glutathione, vitamins C and E) and the results are summarized in Table 4, below.

TABLE 4

| Group Nos. | Glutathione | Vitamin C | Vitamin E |
|---|---|---|---|
| 1 | 22.71 ± 1.73 | 0.838 ± 0.013 | 5.49 ± 0.66 |
| 2 | 17.93 ± 1.08 a*** | 0.692 ± 0.027 a*** | 3.93 ± 0.13 a*** |
| 3 | 20.91 ± 1.70 b*** | 0.836 ± 0.04 b*** | 5.12 ± 0.13 b*** |
| 4 | 22.70 ± 1.53 b*** | 0.836 ± 0.019 b*** | 5.71 ± 0.36 b*** |
| 5 | 14.87 ± 1.49 a*** | 0.593 ± 0.013 a*** | 3.08 ± 0.14 a*** |
| 6 | 18.15 ± 0.78 c*** | 0.767 ± 0.015 c*** | 4.72 ± 0.15 c*** |
| 7 | 19.71 ± 1.02 c*** | 0.804 ± 0.015 c*** | 5.01 ± 0.11 c*** |
| 8 | 9.92 ± 1.16 a*** | 0.545 ± 0.014 a*** | 2.06 ± 0.13 a*** |
| 9 | 16.31 ± 0.93 d*** | 0.664 ± 0.023 d*** | 3.94 ± 0.83 d*** |
| 10 | 18.24 ± 1.47 d*** | 0.762 ± 0.019 d*** | 5.19 ± 0.17 d*** |
| 11 | 23.82 ± 1.36 aNS | 0.835 ± 0.03 aNS | 5.64 ± 0.32 aNS | a: compared to Group 1
b: compared to Group 2
c: compared to Group 5
d: compared to Group 8
***P < 0.001

As seen in Table 4, the rats irradiated with gamma radiation (Groups 2, 5 and 8) showed a sharp decrease in the activity of the non-enzymatic antioxidants (glutathione, vitamins C and E) in comparison with the control (Group 1), but were restored to a near normal state (control) after administration with hesperidin for 7 days (Groups 3, 4, 6, 7, 9 and 10).

These results suggest that hesperidin significantly prevents cell damage by suppressing gamma radiation-induced decreases in hepatic non-enzymatic antioxidants, resulting in cytoprotection.

G. Histological Observation of the Liver

Figure 10:
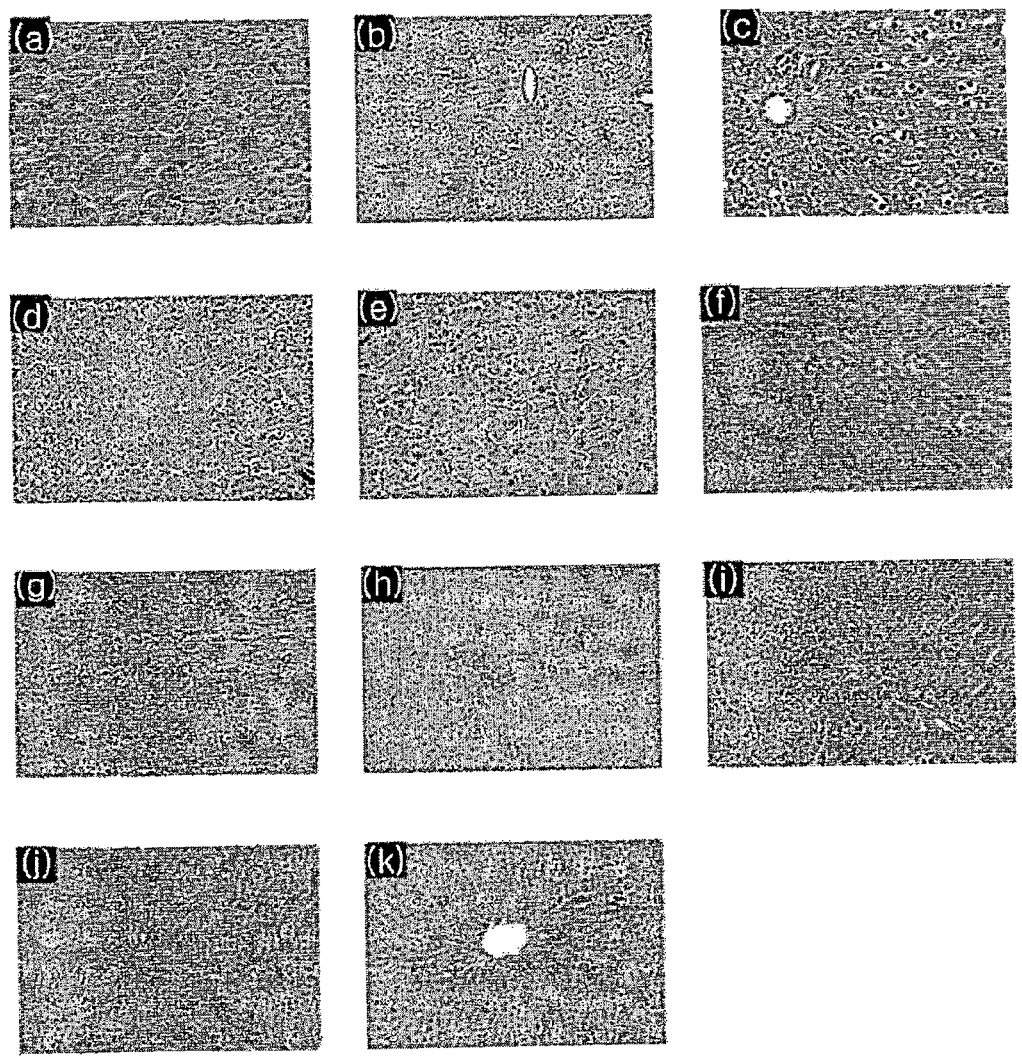
FIG. 10 is of photographs of the livers excised from the rats which were (a) used as a control; (b) exposed to 1 Gy of gamma radiation; (c) treated with hesperidin (50 mg/kg) after exposure to 1 Gy of gamma radiation; (d) treated with hesperidin (100 mg/kg) after exposure to 1 Gy of gamma radiation; (e) exposed to 3 Gy of gamma radiation; (f) treated with hesperidin (50 mg/kg) after exposure to 3 Gy of gamma radiation; (g) treated with hesperidin (100 mg/kg) after exposure to 3 Gy of gamma radiation; (h) exposed to 5 Gy of gamma radiation; (i) treated with hesperidin (50 mg/kg) after exposure to 5 Gy of gamma radiation; (j) treated with hesperidin (100 mg/kg) after exposure to 5 Gy of gamma radiation; and (k) treated with hesperidin (100 mg/kg).

Hepatectomy was performed on rats which were treated with gamma radiation alone or in combination with hesperidin, or which were not treated with radiation but received hesperidin, followed by the histological observation of the livers as photographed in FIG. 10.

FIG. 10(a) is a photograph of the liver excised from a normal rat, showing a normal cellular structure.

FIG. 10(b) is a photograph of the liver excised from a rat exposed to 1 Gy of gamma radiation, showing the expansion of hepatocytes due to the radiation-induced effects including vein thickening, portal vein injury, and regulation fail in cytoplasmic vacuolation and liver plate.

FIGS. 10(c) and 10(d) are photographs of the livers excised from rats treated with hesperidin at a dose of 50 mg/kg (c) and 100 mg/kg (d) for 7 days following exposure to 1 Gy of gamma radiation, showing the protection of the portal vein and the bile duct from injury caused by the radiation.

FIGS. 10(e) to 10(g) are photographs of the livers excised from rats exposed to 3 Gy of gamma radiation and then treated with hesperidin at a dose of 50 mg/kg (f) and 100 mg/kg (g) for 7 days.

As seen in FIGS. 10(e) to 10(g), exposure to the gamma radiation thickens the portal vein, injures the portal vein and induces a control failure in cytoplasmic vacuolation and liver plate, resulting in the expansion of hepatocytes, but treatment with hesperidin was found to reduce these radiation-induced effects.

FIGS. 10(h) to 10(j) are photographs of the livers excised from rats exposed to 5 Gy of gamma radiation, followed by treatment with hesperidin at a dose of 50 mg/kg (i) and 100 mg/kg (j) for 7 days.

As seen in FIGS. 10(h) to 10(j), exposure to the gamma radiation thickens the portal vein, injures the portal vein and induces a control failure in cytoplasmic vacuolation and liver plate, resulting in the expansion of hepatocytes, but treatment with hesperidin was found to reduce these radiation-induced effects.

FIG. 10(k) is a photograph of the liver treated with hesperidin which was without exposure to gamma radiation.

As seen in FIG. 10(k), the hesperidin-treated liver which was without exposure to gamma radiation tissues did not undergo necrosis or apoptosis, and showed hepatocytes without injured cetrilobula regions, normal liver plates and normal epithelial cells in comparison with the control. Thus, administration with hesperidin alone changes almost none of the cellular parameters measured, demonstrating that hesperidin is not cytotoxic.

In accordance with the present invention, therefore, hesperidin is useful as a cytoprotective against radiation because it can protect cells from being injured by radiation such as gamma radiation and gives no cytotoxic effects.

FORMULATION EXAMPLE 1

Preparation of Pharmaceutical Preparation

| 1-1 Preparation of Powder | |
| --- | --- |
| Hesperidin: | 2 g |
| Lactose: | 2 g |

The above ingredients were mixed and loaded into an airtight sac to produce a powder agent.

| 1-2 Preparation of Tablet | |
| --- | --- |
| Hesperidin: | 100 mg |
| Corn Starch: | 100 mg |
| Lactose: | 100 mg |
| Mg Stearate: | 2 mg |

These ingredients were mixed and prepared into tablets using a typical tabletting method.

| 1-3 Preparation of Capsule | |
| --- | --- |
| Hesperidin: | 100 mg |
| Corn Starch: | 100 mg |
| Lactose: | 100 mg |
| Mg Stearate: | 2 mg |

These ingredients were mixed and loaded into gelatin capsules according to a typical method to produce capsules.

| 1-4 Preparation of Injection | |
| --- | --- |
| Hesperidin: | 10 µg/mL |
| Dil. HCl BP: | added to form pH 3.5 |
| NaCl BP injection: | up to 1 mL |

Hesperidin was dissolved in a suitable volume of a NaCl BP injection, and the solution was adjusted to a pH of 3.5 with diluted HCl BP and to a desired volume with an NaCl BP injection, followed by sufficient mixing. The solution was loaded into transparent 5 mL type I ampules, which were hermetically sealed by melting, followed by autoclaving at 120° C. for 15 min to prepare injections.

FORMULATION EXAMPLE 2

Preparation of Health Food 2-1. Preparation of Flour-Based Food

To 100 weight parts of flour were added 0.1~5.0 wt parts of hesperidin according to the present invention and the flour mixture was used to make breads, cakes, cookies and noodles.

2-2. Preparation of Soups and Gravies

Hesperidin according to the present invention was added in an amount of 0.1~5 wt parts to 100 weight parts of typical soups or gravies to prepare health-improving soups or gravies for consumption with meat processed products or noodles.

2-3. Preparation of Dairy Products

To 100 wt parts of milk was added 5~10 wt parts of hesperidin according to the present invention and the milk was used to prepare various dairy products such as butter and ice cream.

2-4. Preparation of Zen Food

Unmilled rice, barley, glutinous ricer and unshelled adlay were pre-gelatinized using a typical method, dried and roasted before grinding into powder with a particle size of 60 meshes.

Black soybean, black sesame and wild sesame were steamed according to a typical method, dried and roasted before grinding into powder with a particle size of 60 meshes.

Hesperidin according to the present invention was concentrated in a vacuum using a vacuum concentrator and dried in a convection oven, followed by grinding into powder with a particle size of 60 meshes.

The powders made of the grains, the seeds, and hesperidin, according to the present invention were formulated at the following ratios to yield a zen food.

Grains (unmilled rice 30 wt parts, unshelled adlay 15 wt parts, barley 20 wt parts), Seeds (wild sesame 7 wt parts, black soybean 8 wt parts, black sesame 7 wt parts), Dry powder of the extract according to the present invention (3 wt parts),

*Ganoderma lucidum* (0.5 wt parts),

Foxglove (0.5 wt parts)

FORMULATION EXAMPLE 3

Preparation of Beverages 3-1. Preparation of health beverage

Liquid fructose (0.5 wt parts), oligosaccharide (2 wt parts), sugar (2 wt parts), salt (0.5 wt parts) and water (75 wt parts) were homogeneously formulated, along with hesperidin (10 wt parts) according to the present invention and the formulation was subjected to pasteurization and loaded into a bottle, such as a glass bottle, a PET bottle, etc.

3-2. Preparation of Vegetable Juice 5 g of hesperidin according to the present invention was added to 1 liter of typical tomato or carrot juice to give a health-improving vegetable juice.

3-3. Preparation of Fruit Juice 1 g of heperidin according to the present invention was added to 1 liter of typical apple or grape juice to give a health-improving fruit juice.

Having the ability to protect cells from radiation-induced injuries in addition to being non-toxic to cells, as described hitherto, hesperidin in accordance with the present invention can be used as an active cytoprotective agent.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for restoring radiation-induced damaged hepatocytes of a subject undergoing radiotherapy against a radiation, consisting essentially of administering hesperidin, represented by the following Chemical Formula 1, or a pharmaceutically acceptable salt thereof in a therapeutically effective amount to the subject in need thereof, wherein the subject in need thereof is exposed to radiation before administration of hesperidin:

<Chemical Formula 1>

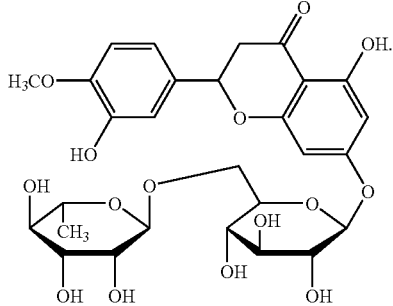

2. The method according to claim 1, wherein the radiation is selected from the group consisting of X ray, α radiation, β radiation, γ radiation and a combination thereof.

3. The method according to claim 1, wherein the method is accompanied by a restoration of a radiation-induced reduction in body weight, liver weight and splenic index.

4. The method according to claim 1, wherein the method is accompanied by a restoration of a radiation-induced increase in activity of a serum marker enzyme.

5. The method according to claim 1, wherein the method is accompanied by a restoration of a radiation-induced reduction in activity of a hepatic tissue marker enzyme.

6. The method according to claim 4, wherein the serum marker enzyme is selected from the group consisting of aspartate transaminase (AST), alanine transaminase (ALT), alkaline phosphatase (ALP), lactate dehydrogenase (LDH), gamma-glutamyl transpeptidase (γ-GT), and a combination thereof.

7. The method according to claim 5, wherein the tissue marker enzyme is selected from the group consisting of aspartate transaminase (AST), alanine transaminase (ALT), alkaline phosphatase (ALP), lactate dehydrogenase (LDH), gamma-glutamyl transpeptidase (γ-GT), and a combination thereof.

8. The method according to claim 1, wherein the method is accompanied by a restoration of a radiation-induced increase in lipid peroxidation within a liver tissue.

9. The method according to claim 1, wherein the method is accompanied by a restoration of a radiation-induced reduction in activity of a hepatic enzymatic antioxidant.

10. The method according to claim 9, wherein the enzymatic antioxidant is selected from the group consisting of superoxide dismutase, glutathione peroxidase (GPx), and a combination thereof.

11. The method according to claim 9, wherein the method is accompanied by a restoration of a radiation-induced reduction in activity of a hepatic non-enzymatic antioxidant.

12. The method according to claim 11, wherein the non-enzymatic antioxidant is selected from the group consisting of glutathione, vitamin C, vitamin E and a combination thereof.

* * * * *